United States Patent [19]

Eriksson

[11] Patent Number: 5,152,757

[45] Date of Patent: Oct. 6, 1992

[54] SYSTEM FOR DIAGNOSIS AND TREATMENT OF WOUNDS

[75] Inventor: Elof Eriksson, Boston, Mass.

[73] Assignee: Brigham and Women's Hospital, Boston, Mass.

[21] Appl. No.: 707,248

[22] Filed: May 22, 1991

Related U.S. Application Data

[63] Continuation of Ser. No. 451,957, Dec. 14, 1989, abandoned.

[51] Int. Cl.⁵ ............................................. A61F 13/00
[52] U.S. Cl. ............................................. 604/305
[58] Field of Search ............... 604/304–308; 424/DIG. 13; 623/15; 128/369, 370

[56] References Cited

U.S. PATENT DOCUMENTS

| | | | |
|---|---|---|---|
| 1,224,862 | 5/1917 | Barker | 604/305 |
| 1,385,346 | 7/1921 | Taylor | 604/305 |
| 1,970,013 | 8/1934 | Makmourian | 128/370 |
| 2,113,253 | 4/1938 | Gray | 128/370 |
| 2,565,751 | 8/1951 | Birkle | 128/370 |
| 3,026,874 | 3/1962 | Stevens | 604/305 |
| 3,089,492 | 5/1963 | Owens | 604/305 |
| 3,288,140 | 11/1966 | McCarthy | 604/289 |
| 3,327,705 | 6/1967 | Miller et al. | |
| 3,366,110 | 1/1968 | Gaylord | 128/369 |
| 3,367,332 | 2/1968 | Groves | 604/305 |
| 3,692,028 | 9/1972 | Etten et al. | 128/369 |
| 3,831,593 | 8/1974 | Ochoa | 128/369 |
| 4,375,812 | 3/1983 | Vaseen | |
| 4,382,441 | 5/1983 | Svedman | 604/305 |
| 4,460,370 | 7/1984 | Allison et al. | 604/93 |
| 4,778,456 | 10/1988 | Lokken | 604/305 |
| 4,784,854 | 11/1988 | Seguin et al. | |
| 4,911,688 | 3/1990 | Jones | 604/305 |

FOREIGN PATENT DOCUMENTS

| | | | |
|---|---|---|---|
| 1444974 | 3/1966 | France | 128/367 |
| 0641061 | 8/1950 | United Kingdom | 604/305 |

Primary Examiner—C. Fred Rosenbaum
Assistant Examiner—Sharon Finkel
Attorney, Agent, or Firm—Kilpatrick & Cody

[57] ABSTRACT

A treatment system according to the invention comprises a chamber, treatment fluid, treatment additives, control over treatment variables and monitoring capabilities. The chamber encloses a predetermined surface area about the wound. The chamber provides protection from the wound from the surrounding non-sterile environment, control of treatment variables, containment for continuous fluid treatment, an effective delivery system, an effective interface between the wound and the environment, direct monitoring of wound physiology and wound diagnosis. The treatment system provides monitoring of the wound which is essential to enhancing the healing process. Monitoring constitutes extraction and analysis of the system fluid and clinical wound diagnosis. The system provides visual monitoring of the wound itself as well as the fluid within the system. The monitoring features of the system, in addition to the precise control over treatment variables, facilitates research.

43 Claims, 10 Drawing Sheets

SYSTEM FOR DIAGNOSIS AND TREATMENT OF WOUNDS

This is a continuation of copending application Ser. No. 07/451,957 filed on Dec. 14, 1989, now abandoned.

BACKGROUND OF THE INVENTION

1. Field of the Invention

The invention relates to a system for diagnosis and treatment of wounds and other skin disorders. More particularly, the invention relates to a treatment system for wounds, burns, skin diseases including tumors and the like, to enhance healing.

2. Related Art

Most open wounds are currently treated with moist or dry gauze. This results in excessive pain, dehydration of the wound, loss of fluids and proteins, loss of heat and delayed healing. In order to delay the appearance of infection, burn wounds are additionally treated with antibacterial creams and the like.

Open wounds appear to heal faster in an environment which is somewhere between moist and dry. Partial thickness wounds heal faster when covered with a polyethylene film than when exposed to air. Conventionally, dressings with some water permeability provide the optimal conditions for healing.

The concept of protecting a wound from the environment and using fluid to treat the wound is generally known. Generally, the broad concept of providing a fluid environment for wounds, burns and the like is known. For example, treating wounds by fluid treatment is disclosed in U.S. Pat. Nos. 3,089,492 to Owens, 3,367,332 to Groves, 4,375,812 to Vaseen and 4,382,441 to Svedman. These references also disclose various techniques to assist in treating a wound. For example, adding a wide range of medicaments to the fluid, controlling temperature, ion concentrations, diffusion and concentration gradients, and osmotic pressure.

Fluid treatment has been recognized as useful in cleansing wounds and removing foreign particles in a "stream" fluid treatment system as taught in U.S. Pat. No. 3,288,140 to McCarthy. Groves utilizes a semi-permeable membrane as part of the bandage (chamber) to allow passage of some matter out of the enclosed environment and Svedman, discussed above, indicates that the system described therein acts to remove degradation products. The system described in Svedman also acts as a transport system for supplying the tissue with nutritive substances. U.S. Pat. No. 4,784,854 to Seguin is just one example of a large number of references which disclose compositions, fluid and otherwise, for application to skin and wounds, for creating an enhanced growth or regenerative environment for tissue.

Apparatus used in connection with fluid treatment systems where wounds are enclosed in a chamber allowing the administration of antibiotics and other medications are also known in the art. For example, the apparatus disclosed by U.S. Pat. No. 3,026,874 issued to Stevens comprises a chamber, a seal between the chamber and the skin, a transparent "window", and an inlet and an outlet port. Groves and Svedman disclose variations on this concept.

However, none of the systems described above have gained clinical acceptance. The prior art apparatus and methods fail to provide the capability to diagnose the condition of the wound. Further, most of the prior art systems were designed for the use of a single treatment modality or single drug treatment which greatly limits their usefulness. None of the prior art references recognize enhanced wound healing or comprehensive control over the wound healing process.

SUMMARY OF THE INVENTION

The present invention overcomes the deficiencies of the prior art and provides a comprehensive treatment system for wounds, burns, skin diseases and the like, to enhance wound healing. A treatment system for wounds and other skin disorders according to the invention comprises a chamber secured about the periphery of a wound, said chamber having portal means for introduction of treatment fluids into the chamber and for extraction of fluid from said chamber, treatment fluid, at least one treatment additive, control means for treatment variables, and monitoring means for monitoring wound conditions. Treatment additives are selected according to wound indications and include growth factors, antibiotics, anesthetics, enzymes and oxygen. Treatment variables are controlled according to wound indications. Examples of treatment variables are temperature, colloid osmotic pressure, ph, ion concentration and oxygen content.

The treatment fluid is selected according to wound indications and may be changed periodically according to wound indications or continuously perfused through the chamber in which case the fluid is treated to decontaminate said fluid and/or fresh treatment fluid is introduced into the system.

Monitoring is accomplished by visual inspection of the wound and the treatment fluid. This may be done through a transparent section of the chamber. Monitoring also includes extracting fluid from the system and analyzing said fluid for protein content and microorganisms.

The chamber may include a flexible sheet material and may be in the form of a tube or bag depending upon the application. The sheet material has a portion which is substantially transparent. The sheet material has a peripheral adhesive surface. A portion of said chamber is self repairing. The chamber may also comprise portal means which may be inlet and outlet ports.

A releasable compartment may be provided within the chamber. A compartment within said chamber having a permeable membrane is also contemplated.

In one aspect of the invention a chamber may include a first annular ring of flexible sheet material having an inner peripheral edge and an outer peripheral edge and having a top and a bottom, a second annular ring of flexible sheet material having an inner peripheral edge and an outer peripheral edge, the inner peripheral edge of the second annular ring secured to the inner peripheral edge of the first annular ring, and a circular piece of flexible sheet material having a peripheral edge secured to the outer edge of the second annular ring to form a collapsible chamber. The bottom of the first annular ring may have an adhesive surface. The circular piece of flexible sheet material may be substantially transparent.

An H-type joint tape is used to secure adjoining chambers. The tape comprising parallel planes of flexible sheet material connected by a bridge, the outer surfaces of the sheet material having an adhesive surface. The bridge is generally made from a flexible material and the bridge may be associated with a stiffening element which may be embedded within said bridge.

A method for treating wounds and other skin disorders according to the invention includes the steps of securing a chamber about the periphery of the wound, introducing a treatment fluid, introducing at least one treatment additive, controlling treatment variables, and monitoring wound conditions. The treatment additives, treatment fluid and control over treatment variables are selected according to wound indications.

The method may also include changing treatment fluid periodically according to wound indications or the treatment fluid may be continuously perfused through the chamber, in which case the treatment fluid is treated to decontaminate said fluid or fresh treatment fluid is introduced.

The method step of monitoring includes visual inspection of the wound and treatment fluid. Analyzing extracted fluid may also be done.

A treatment system for dialysis according to the invention may include a chamber secured about the periphery of a wound, portal means in the chamber for introduction of treatment fluids into the chamber and for extraction of fluid from the chamber, treatment fluid, at least one treatment additive, control means for treatment variables, and monitoring means for monitoring wound conditions. The treatment additives and control of said treatment variables are selected to create a favorable gradient.

A system for anesthetizing intact skin according to the invention comprises a chamber secured about the periphery of the area to be anesthetized, the chamber having means for introduction of treatment fluids into the chamber, treatment fluid, and at least one treatment additive comprising a local anesthetic.

A treatment system for wounds and other skin disorders according to the invention which facilitates research comprises a chamber secured about the periphery of a wound, the chamber having portal means for introduction of treatment fluids into the chamber and for extraction of fluid from the chamber, treatment fluid, at least one treatment additive, control means for treatment variables, and monitoring means for monitoring wound conditions. The monitoring means comprises visual inspection means whereby the wound may be visually observed and said treatment fluid may be visually observed. The monitoring means may also comprise means for extracting fluid from the system and means for analyzing said fluid. In the fluid, chemicals, proteins, cells and microorganisms are analyzed.

BRIEF DESCRIPTION OF THE DRAWINGS

For better understanding of the invention, reference may be made to the accompanying drawings, in which.

DETAILED DESCRIPTION OF THE PREFERRED EMBODIMENTS

The present invention is a system for diagnosis and treatment of wounds. In addition, the treatment system provides protection from the environment to decrease susceptibility to infection and to enhance wound healing. The term "wound" as used herein will refer to a number of conditions including but not limited to burn wounds, incisional wounds, excisional wounds, tumors, skin diseases and other skin disorders. The term "enhanced wound healing" as used herein means accelerated healing, better quality of healing, healing of wounds that would otherwise not heal and the improvement and elimination of other skin conditions. Other skin conditions include conditions normally referred to as cosmetic, such as wrinkles.

Figure 1:
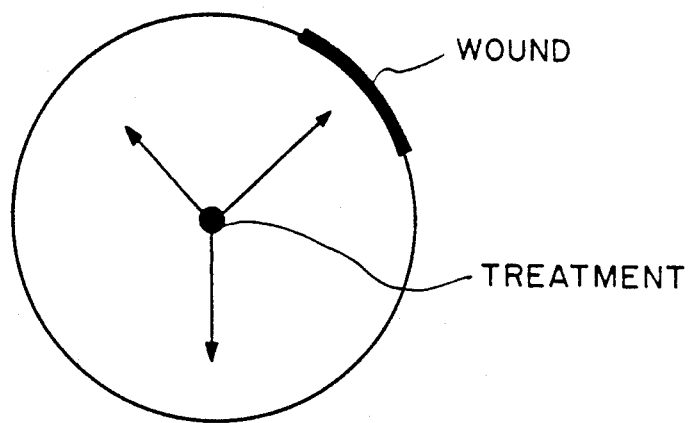
FIG. 1 is a schematic of core treatment.
Figure 2:
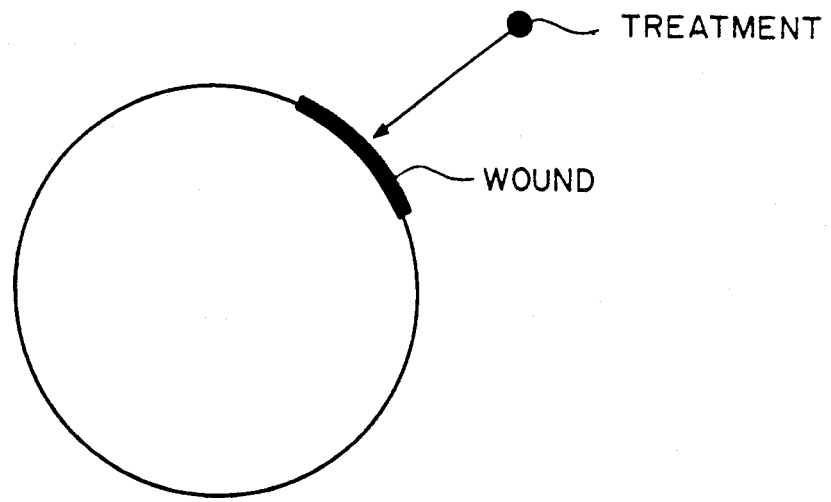
FIG. 2 is a schematic of surface treatment.

The system provides topical treatment rather than ingested or injected treatment, thus allowing greater concentrations and utilization of otherwise toxic materials. Hence, the system provides for direct treatment of the skin surface and the wound surface, and allows for the administration of greater concentrations of medicaments thereby reducing systemic toxicity. For example, before the present invention, most infected wounds were treated with antibiotics by core administration. See FIG. 1, which is a schematic of core administration. As illustrated in FIG. 2, which is a schematic of surface treatment, surface treatment creates a favorable gradient in the opposite direction with maximum concentration in the wound and less systemic toxicity. Thus, systems according to the invention provide a particularly effective delivery system.

The invention is referred to herein generally as a treatment system, but it should be noted that the treatment system is meant to include a method of treatment as well as apparatus for use with such a system. A treatment system according to the invention comprises a chamber, treatment fluid, treatment additives, control over treatment variables and monitoring capabilities. The chamber encloses a predetermined surface area about the wound. The chamber provides protection for the wound from the surrounding non-sterile environment, control of treatment variables, containment for continuous fluid treatment, an effective delivery system, an effective interface between the wound and the environment, direct monitoring of wound physiology and wound diagnosis as well as an exchange similar to dialysis. Another aspect of the treatment system is the use of the treatment system to control pain.

The treatment system provides monitoring of the wound which is essential to enhancing the healing process. Monitoring constitutes extraction and analysis of the system fluid and clinical wound diagnosis. The system provides visual monitoring of the wound itself as well as the fluid within the system. The monitoring features of the system, in addition to providing feedback to assist in the precise control of treatment variables, facilitates research.

Fluid extracted from the system can be analyzed for factors which provide an indication of the status of wound healing and also deleterious factors such as microorganisms, low oxygen, high carbon dioxide and adverse pH. The fluid may be tested for the number and type of bacteria and other microorganisms per cc of fluid, the number and type of cells, the amount and type of proteins, and other factors. Clinical diagnosis of the wound physiology and the patient generally is also arrived at. Immediately upon diagnosis, further treatment of the wound may be started by introducing treatment additives and controlling treatment variables. Analyzing extracted fluid complements visual diagnosis of the wound physiology and general diagnosis of the patient. Depending on the type of wound, the extracted fluid can be tested for: (a) the presence of microorganisms, (b) cells, (c) amount and type of protein, (d) chemicals, (e) oxygen, (f) carbon dioxide levels, and (g) pH. Typically, this data is recorded and used for wound diagnosis. Once diagnosis is complete, fluid treatment intervention is adjusted accordingly.

Additional growth factors that are produced by the wound are also measured when extracted fluid is analyzed. Additional factors tested for are the presence and the amounts of various inflammatory mediators and various antigens. The presence of antigens could serve an important diagnostic purpose and be tested with specific antibodies that would be delivered through the wound chamber. This would give the information about what to replace, how to treat, and would provide monitoring of the improvement of the wound. It is important to note that the chamber establishes an environment that allows the positive factors produced by the body to be present.

The treatment system provides control over treatment variables including temperature, specific ion concentration, colloid osmotic pressure, glucose concentration, amino acid content, fat concentration, oxygen concentration and carbon dioxide concentration and pH. Control over these additional treatment variables can significantly enhance wound healing.

A treatment system according to the invention provides the option of sequential application and/or control of treatment fluid, treatment additives and treatment variables. The sequential application may be predetermined or it may be responsive to monitoring. Subsequent adjustment or changes in treatment fluid, treatment additives and treatment variables can be made responsive to the indications.

Research is facilitated in the sealed sterile environment created by a system according to the invention because (a) there is no contamination from the outside, (b) direct access to wound fluid for diagnostic and monitoring purposes is achieved, (c) the wound condition can be diagnosed without redressing the wound, and (d) direct monitoring of the wound is simplified. Direct monitoring, especially by analyzing extracted fluid, enables researchers to closely follow the wound healing process. Sequencing and timing of interventions is very important to research strategies and the delivery system or interface provided by a system according to the invention offers significant benefits in this regard.

To implement a treatment system according to the invention, a chamber for enclosing a predetermined surface area about the wound is sealed to the skin surface about the wound by means of an adhesive. The chamber has a transparent section for visual wound monitoring, a portal means for introduction of treatment fluid and treatment additives into the chamber and extraction of fluid from the protective chamber, and monitoring means for analyzing extracted fluid for predetermined variables and wound conditions. An appropriate treatment fluid is introduced into the sealed chamber and the treatment fluid comes into contact with the wound. The treatment fluid may be introduced and then extracted in favor of fresh treatment fluid or treatment fluid may be pumped through the chamber. Selected treatment additives may be introduced into the chamber continuously or at a predetermined time or at periodic intervals. Appropriate control of treatment variables is also effected. Monitoring is accomplished by examination of the patient and visual examination of the fluid within the chamber and the wound itself. In addition, samples of fluid are extracted from the chamber for analysis and diagnosis. Intervention and further treatment is based upon the monitoring data. The chamber is removed once sufficient healing of the wound is diagnosed.

Figure 4:
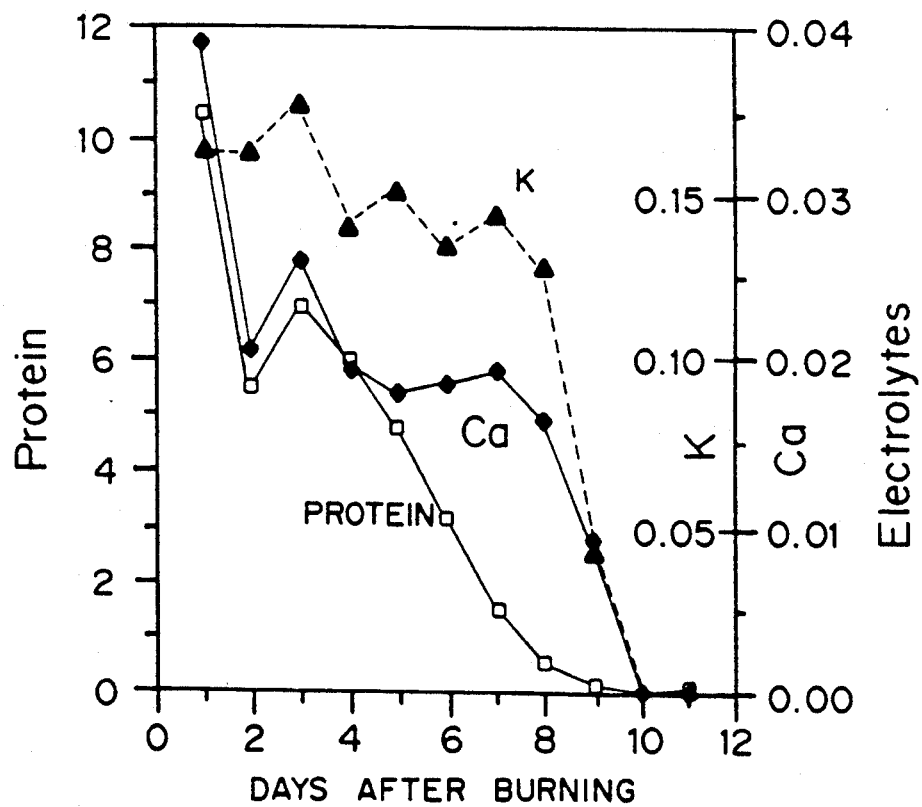
FIG. 4 is a graph of burn protein and electrolyte efflux.
Figure 5:
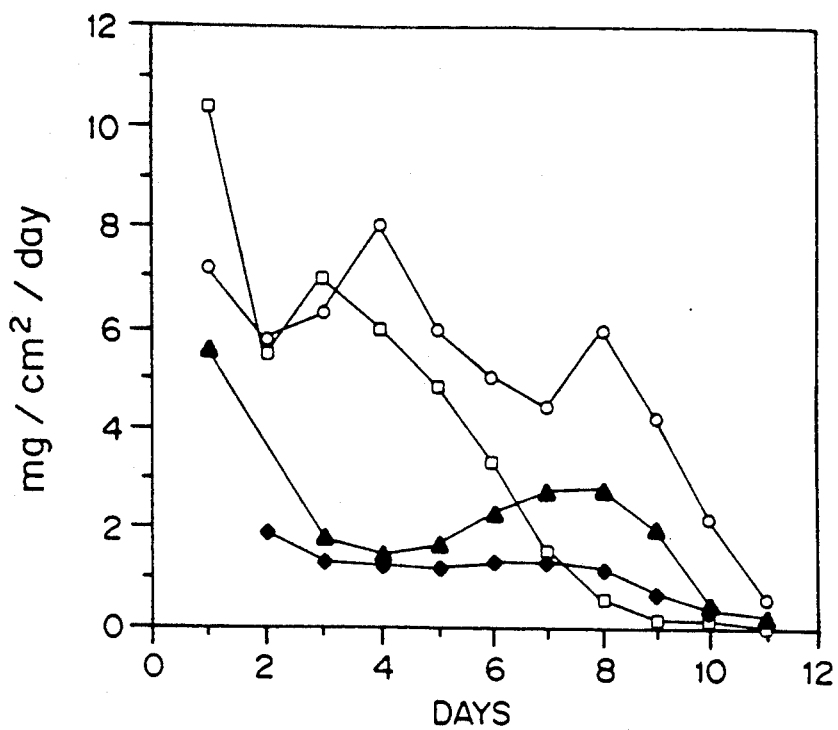
FIG. 5 is a graph of protein efflux from four burns.

To determine whether or not the wound is healed, the protein content of the extracted fluid is analyzed. When the protein content of the extracted fluid decreases to baseline, the wound is healed (FIGS. 4, 5). Methods for determining protein content is well known in the art and are inexpensive and fast. It is also contemplated that the types of protein and the relative amounts of the types of protein may provide further data for monitoring. It is important to note that analyzing the extracted fluid is a non-invasive means of monitoring the healing process as well as a more precise means.

Normal saline is the basic treatment fluid. Buffers may also be part of the basic treatment fluid. For emergency use, it may be kept refrigerated in order to provide the application of a cold liquid. However, generally, the treatment fluid does not require refrigeration. The basic treatment fluid comprises 0.9% sodium chloride with 0.001% lidocaine (10 micrograms per ml). After initial introduction into the treatment system, the treatment fluid is left in place for 2 to 24 hours, depending on wound type. Basic treatment fluid may also comprise penicillin and streptomycin as general antibiotics. Penicillin at 100 IU/ml and Streptomycin at 100 μg/ml provides appropriate concentrations for a general antibiotic component of the treatment fluid.

A variety of treatment additives may be introduced through the chamber into the treatment fluid. Local anesthetics such as lidocaine are utilized for localized pain control. This treatment additive can be used virtually universally in the treatment fluid because allergies to lidocaine are almost nonexistent. Antibiotics for treatment of infection and antimicrobial medication are employed as treatment additives to act against bacteria, fungi or viruses. In the case where such treatment additives are present in prepackaged systems or treatment fluids, caution about the presence of certain antibiotics should be provided. Chemotherapeutics can be directly added to the treatment fluid for tumorous wounds requiring chemotherapy.

The following growth factors have been studied in experimental pig burn wound and excisional wound models as treatment additives: epidermal growth factor (EGF), platelet-derived growth factor (PDGF), insulin-like growth factor (IGF), basic fibroblast growth factor (bFGF), cholera toxin (CT). In all these experiments, all fluids were drained and new fluid was reinjected every 24 hours. The drained fluid was analyzed for protein, potassium, calcium and bacteria. Further analysis of the fluid is used to detect for the presence of growth factors produced by the wound itself.

Tissue culture mediums and fluids which increase oncotic pressure and oxygen accessibility may also be introduced to the chamber as treatment additives.

Selection of treatment additives is wound specific. For example, if an infection has been diagnosed, antibiotics are added in the amount of one single parenteral dose per 1,000 cc of fluid. Furthermore, a treatment additive of gentamicin, tobramycin or carbencillin is appropriate for a wound infection with pseudomonas, detected by analyzing extracted fluid. When hypoxia has been diagnosed, the liquid is passed through an oxygenating chamber before entering the chamber. If a tumor has been diagnosed, chemotherapy is given in an amount of one single parenteral dose per 1,000 cc of fluid. In situations involving a wound containing necrotic tissue and debris, proteolytic enzyme is added to the liquid. Immune modulators are added to the treatment fluid if an inflammatory reaction is exhibited. Epidermal growth factor is added in a concentration of 10 nanograms per cc when required. If the wound is of full thickness without any skin elements in the wound itself, autogenous keratinocytes are harvested from the lower abdomen, minced, trypsinized and injected into the chamber.

When it has been determined that surgical transplantation of skin is necessary, the treatment system only serves as 24 hours of pretreatment for the skin grafting procedure. In instances of large exposed skin areas not yet ready for skin grafting, the treatment system is left in place until such a procedure can take place. If the wound was initially massively infected, samples for analyses of number and type of bacteria, etc., are taken each time the chamber fluid is exchanged. In other skin conditions such as eczema, treatment additives such as cortisone and other immune modulators are added to the treatment fluid. In specific skin conditions, other treatment additives which are commonly used for the treatment of the skin may be introduced into the treatment fluid.

As those skilled in the art will recognize, the invention makes it possible to provide a composition appropriate to the type and condition of wound. Indication Specific Charts 1–11, which follow, represent only an example of the various wounds for which the present system can be used to enhance healing. In the left most column of each indication specific chart is listed the wound type. From left to right the columns provide suggestive treatment fluid, treatment fluid additives and control of treatment variables.

CHART 1

PLASTIC SURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Incisional | Normal Saline with Penicillin & Streptomycin | Immune Modulators Lidocaine Specific antibiotics | q24 h | q24 h | Visual Inspection |
| Burn | Normal Saline with Penicillin & Streptomycin | Immune Modulators Lidocaine Specific antibiotics | 2 hrs - 24 h | 2 | Protein Micro-organisms |
| Traumatic | Normal Saline with Penicillin & Streptomycin | Immune Modulators Lidocaine Specific antibiotics | q6 h | 6 | Protein Micro-organisms |
| Infected | Normal Saline with Penicillin & Streptomycin | Immune Modulators Lidocaine Specific antibiotics | q2 h | 12 | Protein Micro-organisms |
| Diabetic | Normal Saline with Penicillin & Streptomycin | Immune Modulators Lidocaine Specific antibiotics | q12 h | 12 | Protein Micro-organisms |
| Vascular | Normal Saline with Penicillin & Streptomycin | Immune Modulators Lidocaine Specific antibiotics | q12 h | q12 h | Protein Micro-organisms |
| Pressure Sores | Normal Saline with Penicillin & Streptomycin | Immune Modulators Lidocaine Specific antibiotics | q12 h | 12 | Protein Micro-organisms |

CHART 2

ORTHOPEDIC SURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Open Fractures | Normal Saline with Penicillin & Streptomycin | Lidocaine Growth Factors Specific antibiotics | q12 h | q12 h | Protein Micro-organisms |
| Open Joints | Normal Saline | Lidocaine | q12 h | 12 | Protein |

CHART 2-continued

ORTHOPEDIC SURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| | with Penicillin & Streptomycin | Growth Factors Specific antibiotics | | | Micro-organisms |
| Exposed Posthetic Material | Normal Saline with Penicillin & Streptomycin | Lidocaine Growth Factors Specific antibiotics | q12 h | 12 | Protein Micro-organisms |
| Osteo-Myelitis | Normal Saline with Penicillin & Streptomycin | Lidocaine Growth Factors Specific antibiotics | q12 h | 12 | Protein Micro-organisms |
| Traumatic | Normal Saline with Penicillin & Streptomycin | Lidocaine Growth Factors Specific antibiotics | q12 h | 12 | Protein Micro-organisms |
| Incisional | Normal Saline with Penicillin & Streptomycin | Lidocaine Immune Modulators Specific antibiotics | q12 h | q12 h | Visual Inspection |

CHART 3

DERMATOLOGY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Psoriasis | Normal Saline with Penicillin & Streptomycin | Hydrocortisone (1 mg/cc) Non-steroidal anti-inflammatory agents | q12 h | q12 h | Visual Inspection |
| Acne | Normal Saline with Penicillin & Streptomycin | Clindomycin | q12 h | 12 | Micro-organisms |
| Bacterial Infection | Normal Saline with Penicillin & Streptomycin | Specific Antibiotics | q6 h | 6 | Micro-organisms |
| Viral Infection | Normal Saline with Penicillin & Streptomycin | Acyclovir | q12 h | 12 | Antibodies Micro-organisms |
| Benign Neoplasms | Normal Saline with Penicillin & Streptomycin | Keratolytic agents (such as salicylic acid) | q24 h | 24 | Visual inspection |
| Malignant Neoplasms | Normal Saline with Penicillin & Streptomycin | Fluoro-uracil (3 mgs/ml) | q12 h | 12 | Protein Tumor antigens Visual inspection |
| Mycosis Fungoides | Normal Saline with Penicillin & Streptomycin | Hydrocortisone (3 mgs/ml) Bleomycin (1 mg/cc) | q12 h | 12 | Protein Micro-organisms |

CHART 4

CARDIO-THORACIC SURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Open Chest | Normal Saline with Penicillin & Streptomycin | Lidocaine Growth Factors Specific antibiotics | q12 h | q12 h | Protein Micro-organisms |
| Open Empyemas | Normal Saline with Penicillin & Streptomycin | Lidocaine Growth factors Specific antibiotics | q12 h | 12 | Protein Micro-organisms |
| Incisional | Normal Saline with Penicillin & Streptomycin | Lidocaine Immune modulators | q12 h | 12 | Visual |

CHART 5

OTO-RHINO-LARYNGOLOGY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Chondritis of the Ear | Normal Saline with Penicillin & Streptomycin | Lidocaine Growth Factors specific antibiotics | q12 h | q12 h | Protein Micro-organisms |
| Open Wounds | Normal Saline with Penicillin & Streptomycin | Lidocaine Growth factors specific antibiotics | q12 h | 12 | Protein Micro-organisms |
| Incisional | Normal Saline with Penicillin & Streptomycin | Lidocaine Immune modulators | q12 h | 12 | Visual |

CHART 6

NEUROSURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Open Wound | Normal Saline with Penicillin & Streptomycin | Lidocaine Growth Factors specific antibiotics | q12 h | q12 h | Protein Micro-organisms |
| Superficial Brain Abcesses | Normal Saline with Penicillin & Streptomycin | Lidocaine Specific antibiotics Growth factors | q6 h | 6 | Protein Micro-organisms |
| Infected | Normal Saline with Penicillin & Streptomycin | Lidocaine Specific antibiotics Growth factors | q6 h | 6 | Protein Micro-organisms |
| Osteo-Myelitis | Normal Saline with Penicillin & Streptomycin | Lidocaine Specific antibiotics Growth factors | q6 h | 6 | Protein Micro-organisms |

CHART 7

OPHTHALMOLOGY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Bacterial Infection | Normal Saline with Penicillin & Streptomycin | Lidocaine Specific antibiotics Growth Factors | q12 h | q12 h | Protein Micro-organisms |
| Viral Infection | Normal Saline with Penicillin & Streptomycin | Lidocaine Specific antibiotics Antiviral agents Growth factors | q12 h | 12 | Protein Micro-organisms |
| Chemical Burns | Normal Saline with Penicillin & Streptomycin | Lidocaine Growth factors specific antibiotics | q½ h | 12 | Protein Micro-organisms |

CHART 8

VASCULAR SURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Open Fractures | Normal Saline with Penicillin & Streptomycin | Lidocaine Specific antibiotics Growth Factors | q12 h | q12 h | Protein Micro-organisms |
| Exposed Prosthetic Material | Normal Saline with Penicillin & Streptomycin | Lidocaine Specific antibiotics Growth factors | q12 h | q12 h | Protein Micro-organisms |

CHART 9

GENERAL SURGERY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Infected | Normal Saline with Penicillin & Streptomycin | Lidocaine Specific antibiotics | q6 h | q6 h | Bacteria Protein |
| Abcesses | Normal Saline with Penicillin & Streptomycin | Lidocaine Specific antibiotics | q6 h | 6 | Bacteria Protein |
| Incisional | Normal Saline with Penicillin & Streptomycin | Lidocaine Specific antibiotics | q6 h | 6 | Bacteria Protein |

CHART 10

GYNECOLOGY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Vaginal Infection | Normal Saline with Penicillin & Streptomycin | Lidocaine Specific antibiotics Growth factors | q6 h | q6 h | Protein Micro-organisms |
| Superficial Vulvar Infection | Normal Saline with Penicillin & Streptomycin | Lidocaine Specific antibiotics Growth factors | q6 h | 6 | Protein Micro-organisms |

CHART 11

MEDICAL ONCOLOGY

| WOUND TYPE | TREATMENT FLUID | TREATMENT ADDITIVES | FLUID CHANGE | ADDITIVE ADJUSTMENT | MONITOR & ANALYSIS |
|---|---|---|---|---|---|
| Superficial Malignant Tumors | Normal Saline with Penicillin & Streptomycin | Lidocaine | q12 h | q12 h | Protein Micro-organisms |
| Antibiotics to Outpatients | Normal Saline with Penicillin & Streptomycin | Specific antibiotics | q12 h |  | Protein Micro-organisms |

Indication Specific Chart 1 is directed to treatment system examples that can be used in plastic surgery applications depending on the type of wound. An explanation will be given below for a burn wound as listed in the first chart. This explanation can be used to interpret the remaining charts.

A treatment system for the indications noted in Indication Specific Chart 1 - Plastic Surgery may comprise chambers which are pre-packaged or treatment fluid and treatment additives may be introduced from external storage. The selection of the chamber type is wound specific. The treatment fluid comprises saline with a treatment additive growth factor. A combination of EGF and PDGF appears to yield the best results. Possible other treatment additives would include pain medication, antibiotics, and anti-inflammatory agents. For the treatment period of 0–24 hours, treatment additives would include a 100 IU/ml dose of penicillin, streptomycin 100 micrograms/ml, and morphine sulphate 1 ng/ml. As previously noted penicillin and streptomycin may be a standard constituent of treatment fluid. From 24–120 hours penicillin streptomycin, morphine sulphate (EGF-10 ng/ml IGF-20 ng/ml) would be added along with tryptinized keratinozytes at 37 degrees centigrade. The treatment fluid would be changed every 6 to 12 hours for the first 24 hours, daily changing thereafter. Of course, selection and administration of treatment additives is responsive to data gathered in monitoring.

Control over treatment variables would include continuous cooling to 34 degrees centigrade for the first 24 hours. Monitoring would include analyzing extracted fluid for protein and microorganisms, with samples extracted every 24 hours. When the number of microorganisms is less than 10 to the 4th per milliliter or per cc, infection has been resolved. Protein levels checked every day should reach less than 24 mg/dl/cm$^2$.

Indication Specific Charts 2–11 correspond to the following wound types, respectively: Orthopedic surgery; Dermatology; Cardio-Thoracic Surgery; Oto-Rhino-Laryngology; Neurosurgery; Ophthalmology; Vascular surgery; General surgery; Gynecology; and Medical Oncology.

As noted above, portal means provide access for the introduction of treatment fluids and treatment additives into the chamber and extraction of fluid from the chamber. Embodiments allowing treatment fluid to be introduced into the chamber by injection with a conventional hypodermic syringe through a port, the wall of the chamber, or preferably through a self-repairing section of the chamber are contemplated. Extraction of fluid from the chamber may similarly accomplished.

In another contemplated embodiment, the chamber has an inlet and outlet port or separate inlet and outlet ports. Valve mechanisms are, of course, necessary where the apparatus is not to be connected to a treatment fluid reservoir and a drain or connected to a continuous perfusion system. However, in some cases, such as an emergency care version of the system, the ports may be sealed. The apparatus would initially be applied at an accident site and an inner compartment containing treatment fluid opened allowing treatment fluid to enter the chamber. The seals of the ports would be broken at an appropriate time for connection to other apparatus, such as a continuous perfusion system, at a hospital for example.

A preferred embodiment of the treatment system incorporates continuous perfusion of treatment fluid through inlet and outlet ports. A pump or gravity may be used to move the treatment fluid. The treatment fluid may be recirculated after filtering and other appropriate action (e.g. heating or cooling). Alternately, fresh treatment fluid may be introduced and contaminated fluid disposed of.

As noted above, there are a number of treatment variables which may be controlled by the system. One such treatment variable which may be controlled is temperature. It has been found that heating the wound from a temperature of approximately 27° C. (a common temperature of a lower extremity wound) to 37° C. accelerates wound healing. Experimental data has shown that at a wound temperature of approximately 37° C., the rate of wound healing is more than twice as fast as at a temperature of 27° C. The temperature of the wound area can be achieved by heating the treatment fluid. Cooling has also been proven beneficial in the case of acute burn and other traumatic wounds. Cooling reduces pain, swelling and destruction of tissue. In general terms, acute wounds benefit from cooling during the first hours after occurrence of the wound and later, wounds benefit from a temperature of approximately 37° C. Cooling can similarly be effected by cooling the treatment fluid. Generally, a temperature of 20° C. is recommended. In acute traumatic wounds and in burn wounds, a temperature of five degrees centigrade is suggested if the wound area is smaller than ten by ten centimeters. In larger wounds, a cooling temperature of 20° C. is suggested with monitoring of core temperature.

Other treatment variables may also be optimized. Some treatment variables are controlled by introduction of treatment additives, other treatment variables are controlled by extraction of fluid or components thereof, and other treatment variables are controlled by the application of some external control such as heat. For example, ion concentrations can be kept close to extracellular. Colloid osmotic pressure should be maintained at a high level, about 1.5–2 times that of plasma in order to prevent edema formulation. The colloid osmotic pressure of the treatment fluid is generally not adjusted in wounds smaller than ten by ten centimeters. In larger wounds, osmotic pressure is controlled to two times the osmotic pressure of plasma using a Dextran 40 solution.

Glucose, amino acid and fat concentrations should be kept close to that of plasma or corresponding to a skin tissue culture medium. Furthermore, oxygen and carbon dioxide concentrations should be maintained at their normal tissue levels. Oxygen is an effective treatment additive. The addition of oxygen in the chamber is useful in hypoxic wounds. The system also facilitates enzymatic debridement.

Application of the invention can best be understood by using specific examples. Burns cause the burn damaged skin to lose its protective function as the interface between body and environment. The resulting problem is fluid loss and bacterial invasion. A system according to the invention solves this by creating an environment about the wound and maintains only positive factors in the environment.

Such a system was tested on pigs weighing about 40 to 45 kg. Wounds were created under general anesthesia. One square inch burns of partial thickness, and one square inch excisional of partial thickness were created. Treatment with a system corresponding to the present invention was initiated using one square inch chambers. The treatment fluid comprised normal saline with penicillin and streptomycin additives.

Once the treatment was completed, histology revealed less progression of a zone of coagulation in a liquid environment. After four (4) days an air-exposed wound, in which the loosely attached burned epidermal layer was removed immediately after burning, displayed a zone of necrosis extending down from the surface through about the top third to half of the dermis. The same wound exhibited rather extensive scaring after a period of twelve days upon removal of the crusted surface.

Sections taken through the wound center at about four days showed the epidermis invaded by bacteria that had also undermined the crust. At twelve days, the regenerated epithelium was covering the surface but extensive scar tissue containing numerous fibroblasts. Hardly detectable but highly organized collagen bundles were present in residual dermis.

The air-exposed wound were experimentally compared to burn wounds treated with empty or saline-filled chambers. After four days the burn wound developed bacteria-laden debris which covered the crustless surface. Contrastingly, after four days the burn wound covered by a saline-filled chamber displayed no crust, debris and gross signs of wound infection.

Sections taken through the empty-chamber covered burn wound taken at the four (4) day mark revealed necrosis zones much smaller than that of the untreated burn. Numerous bacteria were present. No apparent bacteria were present in a section taken of the saline-treated burn wound and the necrosis zone was very small.

Histology and standardized surface photographs revealed less aberrations (scar) in healing when the liquid treatment was used. After a twelve day period the empty-chamber treated burn wound had reepithelialized but was still somewhat inflamed. The saline wound margins could barely be detected at the twelve day mark.

A section taken through the empty-chamber treated burn wound showed nearly normal epidermis, but also showed hypervascularity and invading bacteria with focal inflammation at twelve days. A similar section through the saline-treated burn wound, although slightly hyperplastic, the epidermis had a normal architecture and a regular stratum corneum. The subepidermal tissue above the dermis was very thin and contained organized collagen, and only a small number of fibroblasts. The histologic appearance was close to that of normal skin.

Control wounds (those in dry air) healed in over twelve days. Wounds enclosed in chambers with air healed in about twelve days. Wounds enclosed in chambers with liquid healed in less than nine days.

Further tests showed that liquids, proteins and ions move across the wound-liquid interface. The volume of chamber fluid above the burn wounds is shown in the graph, FIG. 3. The abscissa is a time line, and the ordinate represents the milliliters of fluid in the chamber. These graphed results represent 95% confidence intervals which are represented on the graph by the number of replicates in parentheses. It is noted that there was no measurable fluid flux across unburned skin.

Figure 3:
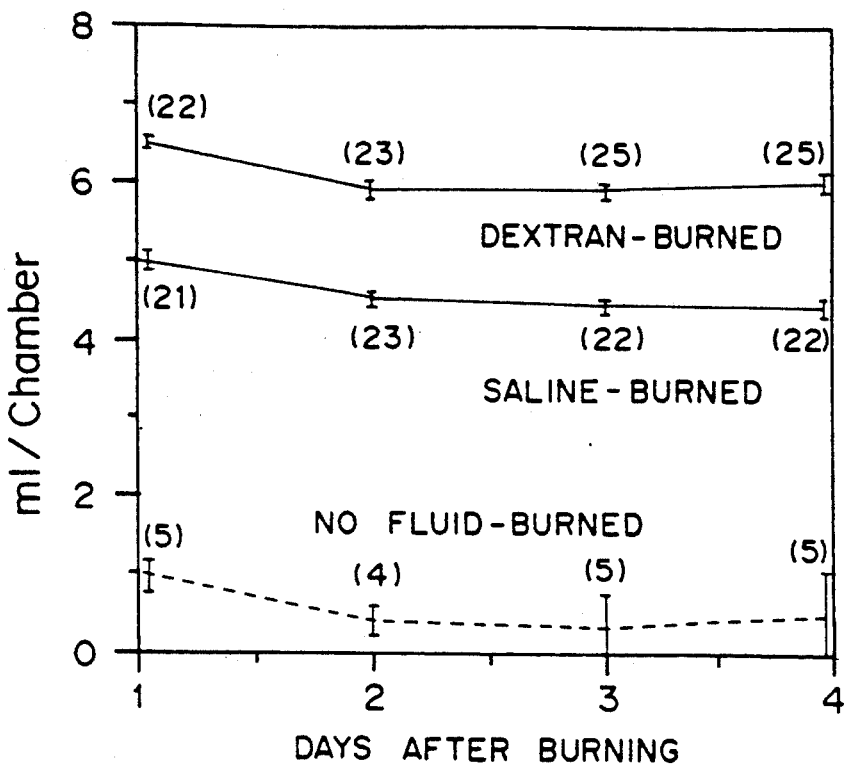
FIG. 3 is a graph of volume of chamber fluid above burn wounds.

Protein and electrolyte efflux for burn wounds is shown in the graph, FIG. 3. Again, the abscissa represents a time line, and in this instance, the leftmost ordinate represents a level of protein and the right ordinate represents both potassium (K) and calcium (Ca) efflux. Protein, K, and Ca were collected daily in saline-filled chambers above a typical burn wound. Protein leakage coincided with an absence of surface epithelium, and protein concentrations in the liquid could be used to monitor wound surface epithelium.

FIG. 4, which is a graph similar to FIG. 3, represents protein collected daily in saline-filled chambers above single burn wounds in four different subjects. Horizontal bars at the bottom represent the efflux through unburned skin.

Figure 6:
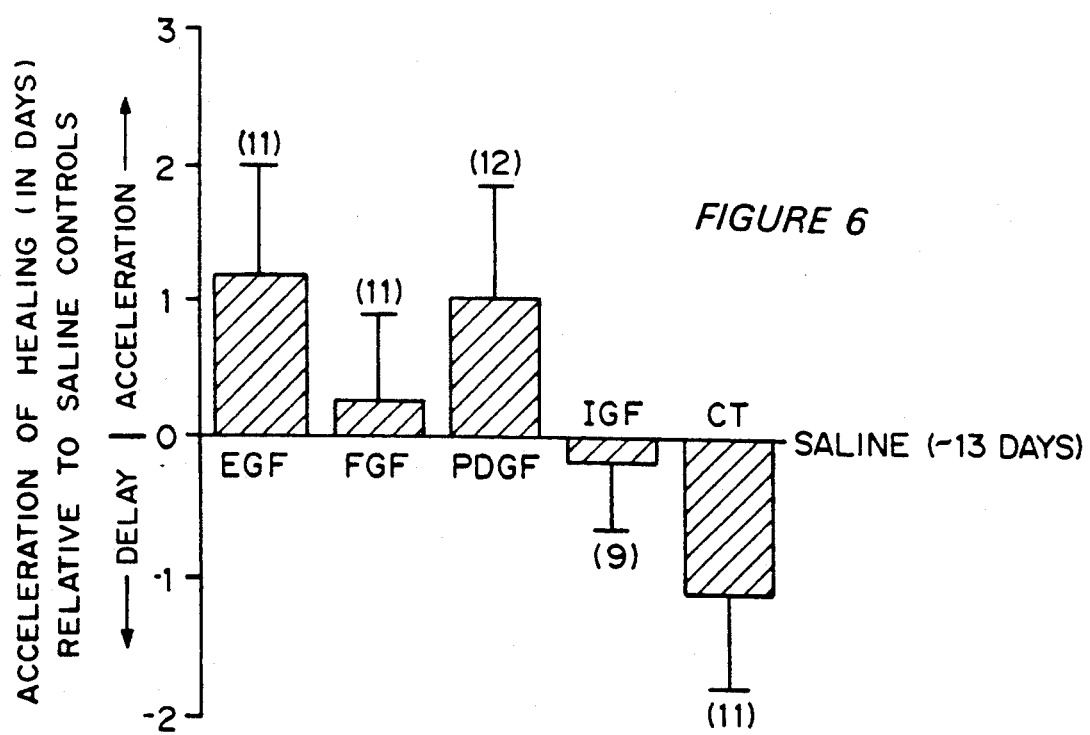
FIG. 6 is a graph of influence of growth factors on burn wound healing times.

The effect of growth factors on the healing times on burn wounds and excisional wounds has also been studied. As shown in FIG. 6, in standardized partial thickness burn wounds in pigs, epidermal growth factor (EGF) and platelet-derived growth factor (PDGF) did reduce the healing time by approximately one day each. Basic fibroblast growth factor (bFGF) and insulin-like growth factor (IGF) had no effect on the healing times. Cholera toxin (CT) increased the healing times by more than one day. In partial thickness excisional wounds in pigs, see FIG. 7, EGF and PDGF were found to reduce healing times while cholera toxin increased the time of healing. bFGF and IGF had no effect.

The system may be used in a variety of applications. As a general drug delivery system, it could be used not only in hospital and outpatient medical settings, but also by individual patients. In the hospital or outpatient medical setting, certain prescription treatment additives may be added as needed. Pre-packaged versions may include specific prescription or non-prescription formulations. The system is very well-suited for emergency care and may be pre-packaged as the apparatus may be packaged for extended storage, rough handling and simple and quick application. The treatment system is also applicable as a wound specific treatment system, where wound treatment fluids, treatment additives and controls for treatment variables are utilized or pre-packaged. Generally the system would be sterilely packed. As mentioned above, the preferred embodiment would not require refrigeration other than for special treatment additives and providing a cold treatment fluid in acute care. UV-light protection may be necessary for special treatment additives.

A preferred embodiment of a chamber 10 employed in the above discussed experiments is shown at FIG. 18. The left-hand illustration is a top view and the right-hand illustration is a side view. The chamber 10 is essentially a bandage having a bellows-type construction. The chamber 10 is constructed of clear vinyl although other plastics and like material are contemplated. Of course, it is necessary to ensure that there is no adverse interaction between treatment fluid, treatment additives or treatment variables and the material selected for the chamber. The bellows fold 12 allows for a large capacity for treatment fluid as well as ease of construction. Essentially, an annular base 14 may be heat (or ultrasound) welded to an annular bellows fold 12 piece and a circular top 16 welded to bellows fold 12 piece. Circular top 16 is a substantially transparent material. The remaining components are not necessarily transparent but may be. A transparent annular base may provide easy visual inspection for leakage. An opening 18 in annular base 14 of approximately 2.5×2.5 cm is provided. Of course, the dimensions and basic materials used to fabricate chamber 10 depend on the application and will be apparent to those skilled in the art. The bottom side 15 of annular base 14 is provided with an adhesive tape or coating suitable for securing the chamber to skin. As those skilled in the art will readily recognize, a removable sheet for protecting the adhesive and maintaining the sterility of the interior of the chamber is desirable. The chambers may be stored in a sterile pack for years. This chamber can take many shapes in order to fit wounds from the size of one square centimeter up to the size of a whole extremity. It is important that the adhesive surface be sufficient to secure the bandage to the skin surface to ensure a leak-proof seal.

As previously mentioned, treatment fluid and treatment additive introduction and subsequent extraction may be accomplished directly through the chamber walls by a needle and syringe. A self-repairing material to construct chamber 10 is contemplated. An alternative method would be to use inlet and outlet ports allowing the introduction and extraction of various substances into the chamber.

A multi-compartmental chamber is also contemplated where a compartment within the chamber would contain treatment fluid. A release mechanism would allow the treatment fluid to enter the main part of the chamber after the chamber was secured to the patient. Further compartments within the chamber may be provided with treatment additives. A compartment which contains a chemical or electrochemical heating or cooling system may also be provided to effect treatment variable control. Prepackaging of a system is especially useful for emergency care applications as well as over-the-counter versions. A skin-cleaning set may be provided together with such a system in order to ensure a leak-free seal between the chamber and the skin. An outer covering for "field" protection would also be available.

The shelf-life of a prepackaged system would only be limited by the selection of treatment fluid and treatment additives. The chamber and treatment additives such as pain medication and antibiotics would be stable for years if provided unmixed in a dry compartment together with a separate compartment for a treatment fluid such as saline. If treatment fluid and treatment additives were premixed in a compartment together, the system would only be stable for approximately several months.

Wound specific treatment systems can be provided for hospital, outpatient medical treatment, home care and emergency care. Specific treatment fluids and treatment additives would be selected and contained within compartments in the chamber or available for introduction into the chamber.

The system would consist of a sterile packaged wound chamber. A preferred embodiment of the chamber would contain at least two compartments. After cleaning the wound and the area where the chamber is to be applied and applying the chamber, a release system is employed to connect the compartments of the chamber and put the liquid and the additives in contact with the wound. If additional substances were to be included, they would either be dissolved in the liquid or the chamber would have an additional compartment where the drugs would be stored dry. There would be an outer protective bandage available which would provide protection in, for instance, field use and when the patient is ambulatory.

Specific instructions about the use in each indication would be provided. For the wound-specific treatment systems which are intended to be used by physicians and nurses, an accompanying video tape is suggested for instruction in these specific applications.

Figure 8A:
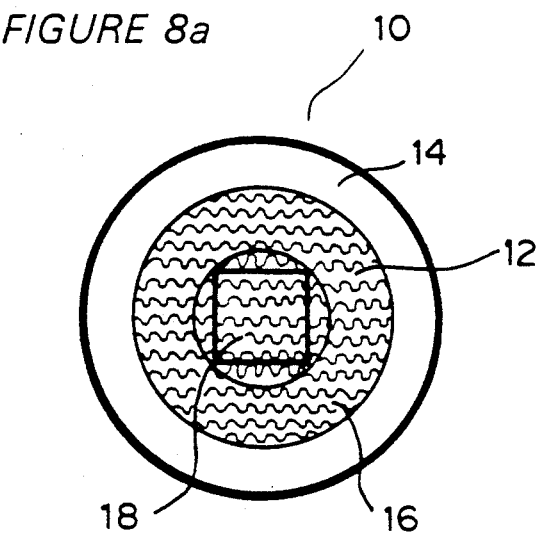
FIG. 8 is an illustration of a preferred embodiment of a chamber according to the invention.
Figure 8B:
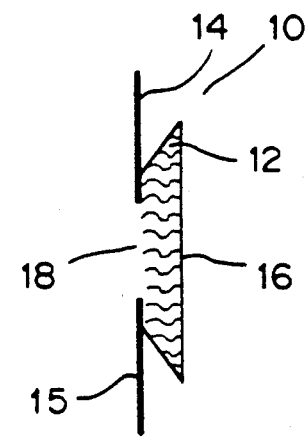
Figure 9:
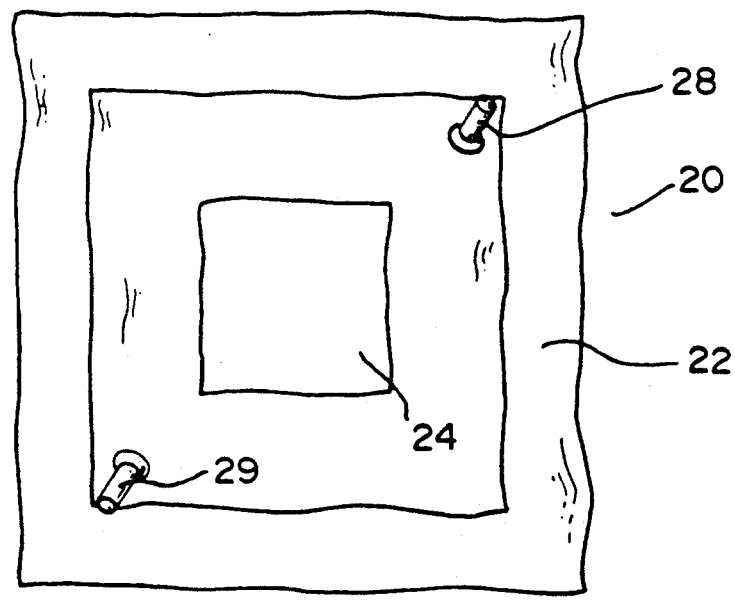
FIG. 9 is an illustration of another preferred embodiment of a chamber according to the invention.

The system also has application as a general drug delivery system. Skin permeability increases with hydration. Thus, with an apparatus according to the invention in place over intact skin, various drugs can be administered without ingestion or injection. Small molecule drugs such as local anesthetics, cortisone, morphine, insulin, antibiotics and the like are particularly suitable for use with a general drug delivery system. A chamber, such as the one illustrated in FIG. 8 or FIG. 9 is secured to the skin of the patient in a suitable location. Treatment fluid is introduced into the chamber and the drug to be administered is then introduced into the chamber. Those of skill in the art will of course recognize that there are advantages to waiting a predetermined time before introducing the drug so as to allow the skin to hydrate. An enzyme which destroys the outer epidermal layer may also be introduced as a treatment additive to increase the rate of penetration. The chamber utilized may also be of the prepackaged type, with the treatment fluid and drug (treatment additive) in releasable compartments.

As previously noted, the system provides an exchange similar to dialysis. Thus, the system can be utilized to facilitate removal of toxic or deleterious substances from the body. As noted above, the permeability of intact skin increases when the skin is hydrated. Treatment additives can be introduced to increase the effectiveness of the system. As with using the treatment system as a general drug delivery system, an enzyme which destroys the outer epidermal layer may be used as a treatment additive in the case when the treatment system is used per dialysis. Other treatment additives may be used to adjust the osmotic gradient across the skin-fluid interface.

In another embodiment particularly useful in prepackaged versions of the system, a permeable or semipermeable container may be formed as part of the chamber as a compartment. The interior wall of the compartment is formed from a permeable or semipermeable material. A suitable non-permeable cover which can be removed before application of the chamber or released after application of the chamber may be employed to protect the membrane and the contents of the compartment. The outer wall of the compartment may be fitted with a portal such as an inlet port so that additional treatment additive may be added.

A preferred embodiment of a system according to the invention is a delivery system for local anesthesia for intact skin. Such a system is particularly useful for preparing a patient for injection or drawing blood. Of course, it is especially useful when the patient is a child. A pre-packaged system having a chamber such as bellows bandage type chamber 20 and a releasable compartment containing 2-6 ccs of lidocaine 5% as the treatment fluid. The efficacy of lidocaine in anesthetizing intact skin has been documented. However, a practical delivery system has previously been lacking. Approximately four hours before the injection procedure, the chamber is applied to the area designated for injection and the treatment fluid allowed to enter the chamber from the releasable compartment. Alternately, a 1% solution of dyclonine administered as a treatment additive for only twenty to thirty minutes is especially effective as a local anesthetic. Benzocaine, in about a 20% solution, is also applicable as a local anesthetic treatment additive.

In another embodiment of the invention, a time release system is provided. Treatment additives with or without a suitable carrier may take the form of pellets or other similar packaging that allows the treatment additive to be dissolved into the treatment fluid over time. Thus, a treatment additive pellet may be introduced into a chamber containing treatment fluid and the treatment additive pellet will dissolve over time thereby increasing treatment additive concentration or replacing depleted treatment additive. Instead of forming treatment additive or treatment additive with a carrier into a pellet form, the treatment additive may be placed into a permeable or semi-permeable container. The container then allows treatment additive to dissolve into the treatment fluid. Selection of the permeable material may be made such that treatment additive only enters the treatment fluid when the balance of treatment additive in the treatment fluid falls below a certain concentration or when some other factor, such as temperature or pH, acts on the container to allow treatment additive to dissolve into the treatment fluid. A natural feedback system for introducing the desired treatment additive is thereby created.

Control over pH may be effectively controlled in this manner. Buffering of the fluid in the treatment system is important and this is one approach to addressing the problem. Other approaches to this problem include making the quantity of treatment fluid so large so as to minimize the effect or so small that the wound fluid can provide the buffer.

Figure 10:
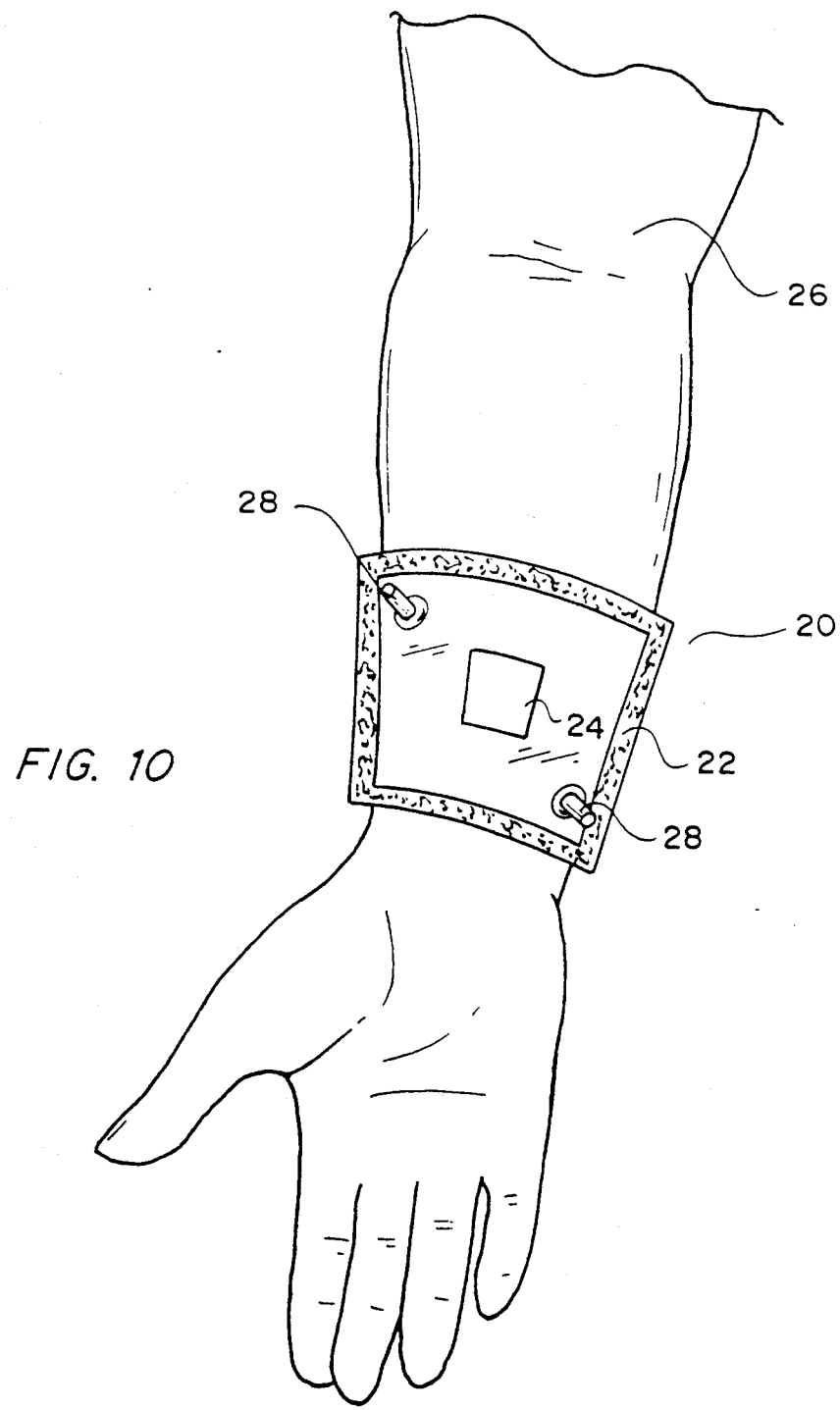
FIG. 10 is an illustration of the embodiment shown in FIG. 9 being set in place on a patient's limb.

Another preferred embodiment of a chamber 20 according to the invention is illustrated in FIG. 9. FIG. 10 shows chamber 20 secured to a limb 26. Chamber 20 is constructed of vinyl or other suitable material. An adhesive periphery 22 is provided and the central portion 24 at least is substantially transparent. As previously noted, the chambers according to the invention are provided with inlet port 28 and outlet port 29. This fitting is well known to those skilled in the art. Essentially, a secure attachment must be made between the fitting and the chamber. It is contemplated that some chambers may be provided only with a single port for both inlet and outlet. Alternately, the port may only allow the introduction of substances via a one-way valve. Extraction of fluid may, in such a case, be accomplished with a syringe or at such time as the chamber is removed. It is further contemplated that separately fittings for ports may be attached to a chamber before or during the time the chamber is secured to the patient.

Fittings appropriate for inlet and outlet ports are shaped and configured for connection to tubing that may be part of a fluid introduction or extraction system, including a continuous perfusion system.

Figure 7:
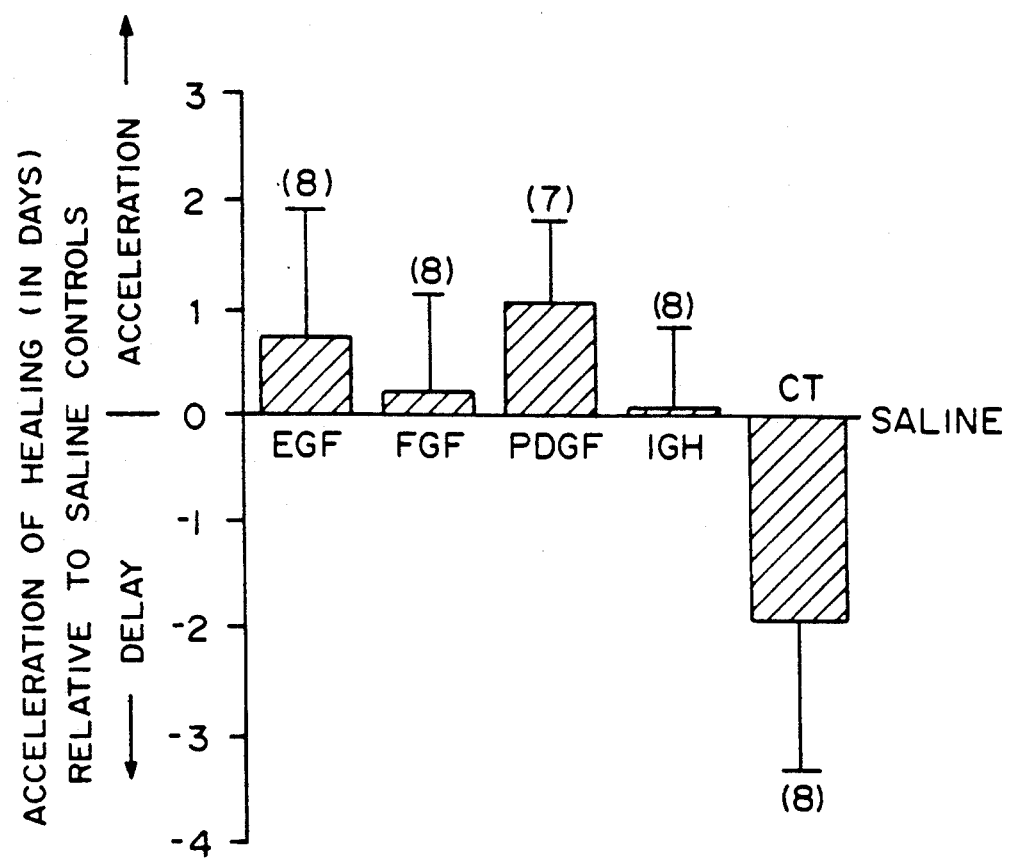
FIG. 7 is a graph of influence of growth factors on excisional wound healing times.
Figure 11:
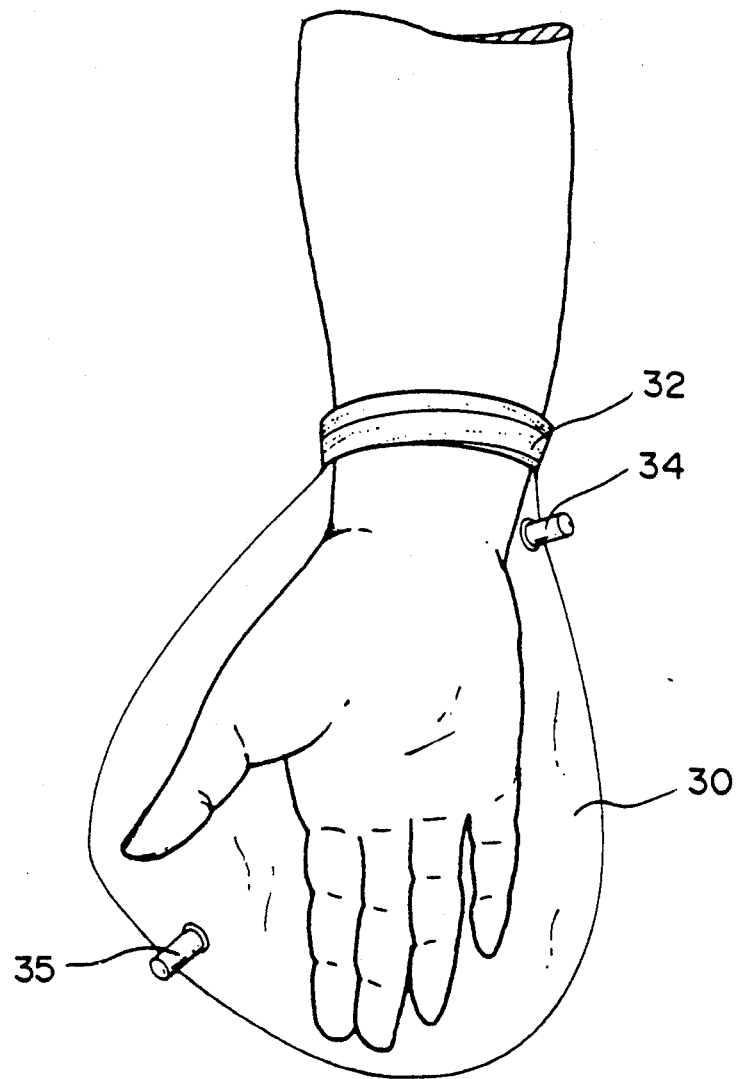
FIG. 11 is an illustration of another preferred embodiment of a chamber according to the invention.

FIG. 11 illustrates another preferred embodiment of the invention with particular application where the distal end of a limb is affected and attachment of a chamber 10 or chamber 20 as shown in FIGS. 6 and 7 respectively is impractical. A chamber 30 constructed of a substantially transparent flexible and resilient material has a cuff 32 provided with an adhesive liner. Inlet and outlet ports 34 and 35 are provided.

Figure 12A:
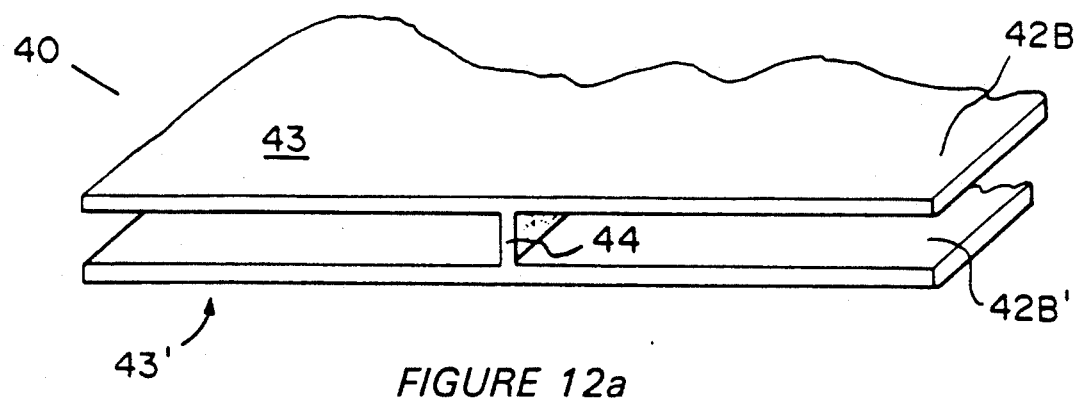
FIG. 12a is a perspective view of an H-type joining tape for use with the embodiment shown in FIG. 13.
Figure 12B:
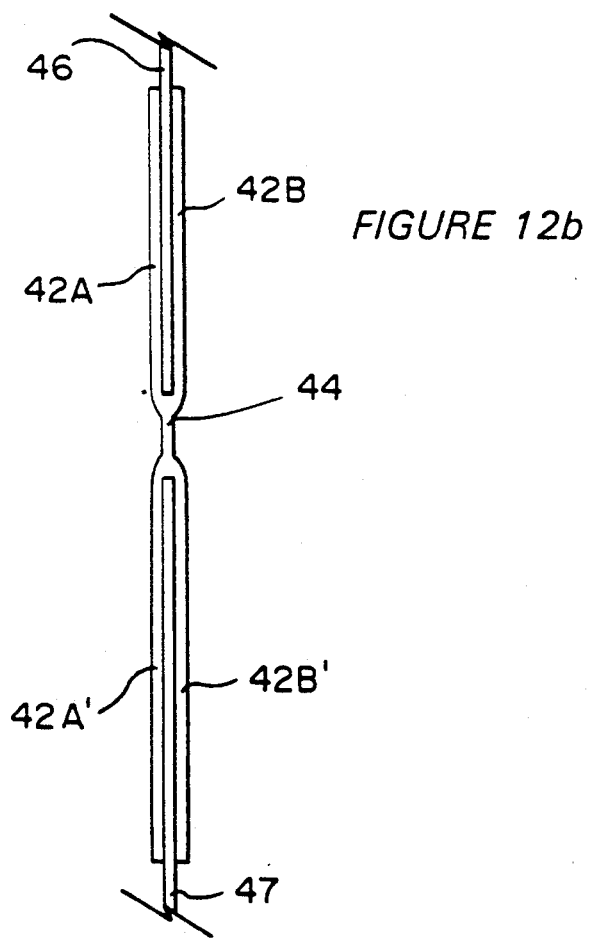
FIG. 12b is a cross-section of an H-type joint tape joining two sections of chambers.
Figure 13:
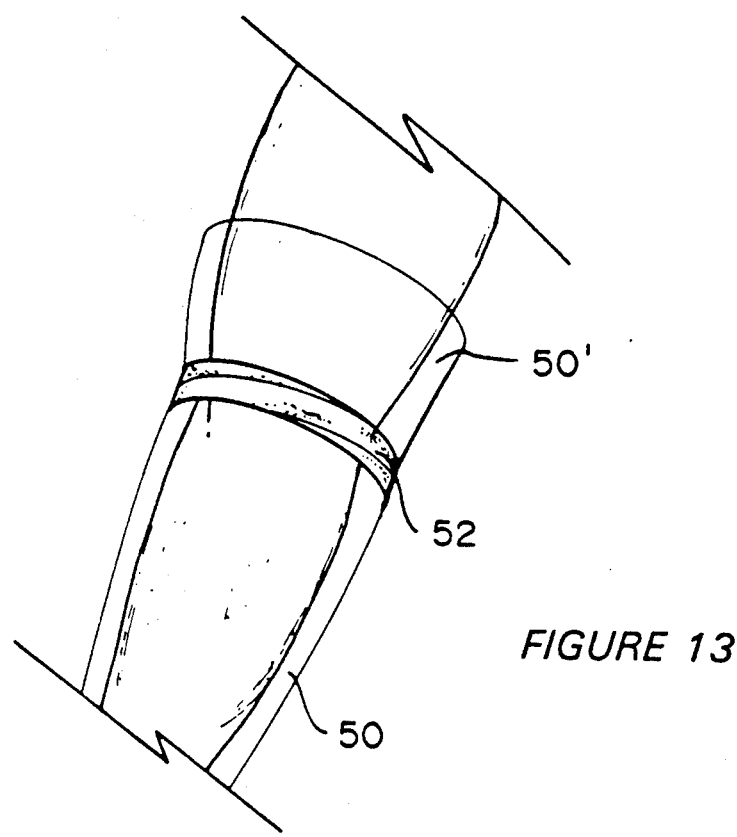
FIG. 13 is an illustration of two chamber sections in place about the limb of a patient.
Figure 14:
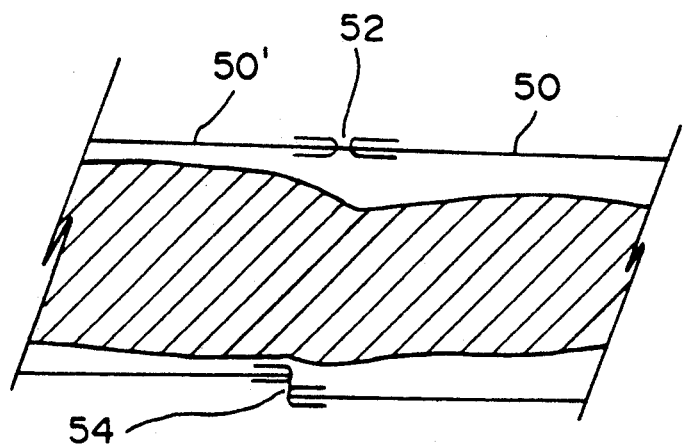
FIG. 14 is a schematic cross-section of the two chamber sections illustrated in FIG. 13 (note that the H-type joining tape is exaggerated for illustration purposes)

Tubular chambers 50 and 50' as illustrated in FIGS. 13 and 14 may be used to extend chamber 30 further to the proximate end of a limb. A novel H-type joint tape 40 is illustrated in FIG. 12a and 12b for joining tubular chambers. The H-type joint tape may also be used to secure a chamber to a patient's skin. The H-tape is designed is to provide flexibility in the design of the wound specific chamber because the size and shape of wounds vary significantly. Wounds to limbs are also commonplace and may involve a large part of a limb.

The H-type joint tape may be fabricated using a suitable flexible and resilient material, similar to that used for the chambers. The H-type joint tape may be manufactured by extrusion in addition to being formed from sheet material. The H-type joint tape includes legs 42a, 42b, 42a', and 42b', a connecting bridge 44, and adhesive surfaces 43 on one side of legs 42. Removable protective coverings are contemplated for adhesive surfaces 43. A preferred embodiment of H-type joint tape has a width of approximately six centimeters, that is, legs 42 and 42' are approximately six centimeters, and the connecting bridge is approximately one centimeter. Of course, those skilled in the art will recognize that these dimensions can be varied to suit a given application for the H-type joint tape. It is important that connecting bridge 44 be securely fixed to legs 42 and 42'.

Legs 42a and 42b fold along a line coextensive with connecting bridge 44 so as to sandwich the edge of a chamber such as tubular chamber 50 between adhesive surface 43. Similarly, legs 42a' and 42b' are folded to sandwich the edge of the adjoining chamber. FIG. 14b illustrates a cross-section (without sectional lines for clarity) showing H-type joint tape 40 secured to edge 46 of a chamber and edge 47 of a chamber. One of the adhesive surfaces may in the alternative be used to secure a chamber to the skin of the patient.

FIG. 13 illustrates two tubular chambers 50 and 50' joined by H-type joint tape 52. Such tubular chambers may be used to extend a chamber along a limb. FIG. 14 illustrates a schematic cross section of the tubular chambers 50 and 50' shown in FIG. 13. Please note that H-type joint tape 52 is exaggerated to illustrate the connection of the H-type joint tape to the chambers. Reference character 54 is present to direct attention to the degree of flexibility necessary to the H-type joint tape.

Figure 15:
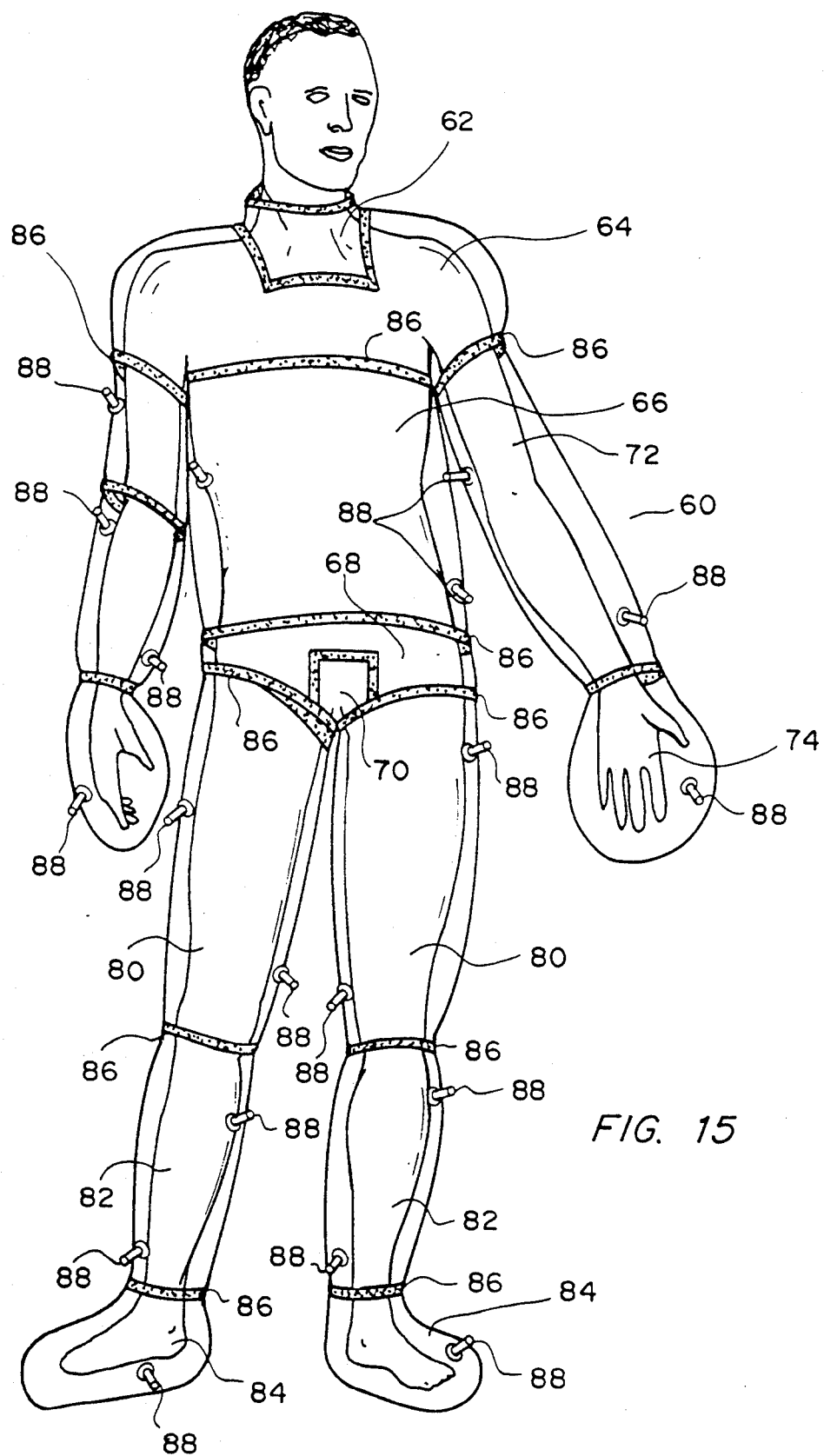
FIG. 15 is an illustration of another preferred embodiment of the invention.

FIG. 15 illustrates a plurality of chambers forming a treatment system body suit 60. Chambers may be formed in a variety of patterns and configurations to cover a body or part of a body. H-type joint tape 86 is used to join adjoining chambers and inlet or outlet ports 88 are provided at various convenient locations. A treatment system body suit 60 is especially useful in the treatment system application for dialysis.

Before applying a chamber to a patient, the skin about the wound is first clipped and shaved. It is scrubbed with Betadine soap for three minutes, after which the area is dried and Betadine solution is applied for three minutes. The skin is then treated with trichlorethane for one minute. After this, a medical liquid adhesive (acrylic, Hollister) is then painted onto the area surrounding the wound where the device is going to be attached. Finally, the backing of the adhesive surface of the device is removed and the device is applied over the wound by pressing on the adhesive surface.

While a treatment system has been described herein and examples provided, numerous modifications and variations of the present invention are possible as will be recognized by those skilled in the art.

What is claimed is:

1. A treatment system for wounds, said treatment system comprising:
   a flexible, conformable chamber having a bellows configuration and sealable about the periphery of a wound so that the chamber surface does not contact the wound;
   a fluid equivalent to 0.9% saline containing adequate oxygen, low levels of carbon dioxide, and a physiological pH suitable for wound healing within the chamber; and
   monitoring means for assessing wound conditions, wherein the chamber provides control over oxygen concentration, carbon dioxide, and pH.

2. The treatment system according to claim 1 further comprising a treatment additive selected according to wound indications from the group consisting of anesthetics, antibiotics, chemotherapeutics, growth factors, cell culture medium, cells, oxygen, buffering agents, enzymes, and immune modulators.

3. The treatment system according to claim 1 further comprising control means for treatment variables selected from the group consisting of temperature, colloid osmotic pressure, pH, ion concentration, and oxygen content.

4. The treatment system according to claim 2 wherein said treatment fluid is selected according to wound indications.

5. The treatment system according to claim 4 further comprising portal means for introduction of treatment fluids into the chamber and for extraction of fluid from said chamber wherein said treatment fluid is changed periodically according to wound indications.

6. The treatment system according to claim 5 wherein said treatment fluid is continuously perfused through said chamber.

7. The treatment system according to claim 6 wherein said treatment fluid is treated to decontaminate said fluid.

8. The treatment system according to claim 7 wherein fresh treatment fluid is introduced into the system.

9. The treatment system according to claim 1 wherein said monitoring means comprises visual inspection means whereby the wound may be visually observed and said treatment fluid may be visually observed.

10. The treatment system according to claim 9 wherein said visual inspection means comprises a transparent section of said chamber.

11. The treatment system according to claim 1 wherein said monitoring means comprises means for extracting fluid from the system and means for analyzing said fluid.

12. The treatment system according to claim 11 wherein said extracted fluid is analyzed for protein content.

13. The treatment system according to claim 11 wherein said extracted fluid is analyzed for microorganisms.

14. The treatment system according to claim 1 wherein said chamber has an adhesive on the surface contacting the periphery of the wound.

15. The treatment system according to claim 1 wherein the chamber comprises a material which is self repairing to allow injection or extraction of material through the chamber walls by a needle.

16. The treatment system according to claim 5 wherein said portal means comprises at least one inlet and outlet port.

17. The treatment system according to claim 1 further comprising a second compartment adjacent the fluid-filled chamber having a connection thereto from which a treatment additive can be released into said fluid-filled chamber.

18. The treatment system according to claim 1 wherein said chamber further comprises a compartment within said chamber, said compartment having a permeable membrane.

19. The treatment system according to claim 1 wherein said chamber comprises a:
- a first annular ring of flexible sheet material having an inner peripheral edge and an outer peripheral edge and having a top and a bottom;
- a second annular ring of flexible sheet material having an inner peripheral edge and an outer peripheral edge, said inner peripheral edge of said second annular ring secured to said inner peripheral edge of said first annular ring; and
- a circular piece of flexible sheet material having a peripheral edge secured to said outer edge of said second annular ring;
whereby a collapsible chamber is formed.

20. The treatment system according to claim 19 wherein the bottom of said first annular ring has an adhesive surface.

21. The treatment system according to claim 20 wherein said circular piece of flexible sheet material is substantially transparent.

22. The treatment system according to claim 19 wherein at least a portion of said chamber is self repairing.

23. The treatment system according to claim 19 wherein said chamber further comprises portal means.

24. The treatment system according to claim 23 wherein said portal means comprises at least one inlet and outlet port.

25. The treatment system according to claim 19 wherein said chamber further comprises a releasable compartment within said chamber.

26. The treatment system according to claim 19 wherein said chamber further comprises a compartment within said chamber, said compartment having a permeable membrane.

27. The treatment system according to claim 1 wherein the periphery of the surface of the chamber contacting the periphery of the wound further comprises a H-type joint tape, said tape comprising parallel planes of flexible sheet material connected by a bridge, the outer surfaces of said sheet material having an adhesive surface.

28. The treatment system according to claim 1 wherein the fluid-filled chamber further comprises a fastener for joining more than one fluid-filled chamber to each other comprising;
- a first attachment strip having an adhesive side and an opposing side secured to a first chamber;
- a second attachment strip having an adhesive side and an opposing side secured to a second chamber; and
- a bridge having one edge secured to the nonadhesive side of said first attachment strip and the other edge secured to the nonadhesive side of said second attachment strip.

29. The treatment system according to claim 27 or 28 wherein said strips and said bridge are a flexible material.

30. The treatment system according to claim 29 wherein said bridge is associated with a stiffening element.

31. The treatment system according to claim 30 wherein said stiffening element is embedded within said bridge.

32. The system of claim 1 for delivering drugs to a patient further comprising in the fluid-filled chamber a drug to be delivered to the wound.

33. The treatment system according to claim 2 wherein said treatment additive is analogous skin cells.

34. A method for treating wounds, said method comprising the steps of:
- securing a fluid-filled, flexible, conformable chamber having a bellows configuration and sealable about the periphery of the wound so that the chamber surface does not contact the wound, wherein the chamber provides control over oxygen concentration, carbon dioxide, and pH;
- introducing into the chamber a treatment fluid equivalent to 0.9% saline containing adequate oxygen, low levels of carbon dioxide, and a physiological pH suitable for wound healing; and
- monitoring wound conditions.

35. The method according to claim 34 further comprising a treatment additive selected according to wound indications from the group consisting of anesthetics, antibiotics, chemotherapeutics, growth factors, cell culture medium, cells, oxygen, buffering agents, enzymes, and immune modulators.

36. The method according to claim 34 further comprising controlling treatment variables selected from the group consisting of temperature, colloid osmotic pressure, pH, ion concentration, and oxygen content according to wound indications.

37. The method according to claim 35 wherein the chamber further comprises portal means for introduction of treatment fluids into the chamber and for extraction of fluid from said chamber, wherein said treatment fluid is changed periodically according to wound indications.

38. The method according to claim 34 wherein said treatment fluid is continuously perfused through said chamber.

39. The method according to claim 38 wherein said treatment fluid is treated to decontaminate said fluid.

40. The method according to claim 38 wherein fresh treatment fluid is introduced into the system.

41. The method according to claim 34 wherein monitoring comprises visual inspection of the wound and treatment fluid.

42. The method according to claim 34 wherein monitoring comprises extracting fluid from the chamber and analyzing said fluid.

43. The treatment system according to claim 37 for dialysis wherein said treatment additives and control of said treatment variables are selected to create a favorable gradient.

* * * * *